(12) United States Patent
Chopra et al.

(10) Patent No.: US 9,101,752 B2
(45) Date of Patent: Aug. 11, 2015

(54) COMPUTER CONTROLLED FOCUSED ULTRASOUND POSITIONING SYSTEM FOR SEQUENTIAL BEAM EMITTING TO SONICATE DISCRETE AND INTERLEAVED TISSUE LOCATIONS

(75) Inventors: Rajiv Chopra, Toronto (CA); Kullervo Hynynen, Toronto (CA); Anthony Chau, Toronto (CA); Adam Christian Waspe, East York (CA)

(73) Assignee: SUNNYBROOK HEALTH SCIENCES CENTRE, Toronto, ON (CA)

( * ) Notice: Subject to any disclaimer, the term of this patent is extended or adjusted under 35 U.S.C. 154(b) by 961 days.

(21) Appl. No.: 12/618,824

(22) Filed: Nov. 16, 2009

(65) Prior Publication Data

US 2010/0125192 A1      May 20, 2010

Related U.S. Application Data

(60) Provisional application No. 61/115,178, filed on Nov. 17, 2008.

(51) Int. Cl.
*A61B 5/055*      (2006.01)
*A61N 7/02*       (2006.01)
(Continued)

(52) U.S. Cl.
CPC .......... *A61N 7/02* (2013.01); *A61B 8/0816* (2013.01); *A61B 19/22* (2013.01);
(Continued)

(58) Field of Classification Search
CPC .............. A61B 19/22; A61B 2017/00106; A61N 7/02
USPC ......... 429/93.7; 600/411, 415, 437–439, 459; 601/2, 3; 606/27, 28
See application file for complete search history.

(56) References Cited

U.S. PATENT DOCUMENTS

| 5,247,935 A | 9/1993 | Cline et al. |
| 5,275,165 A | 1/1994 | Ettinger et al. |

(Continued)

FOREIGN PATENT DOCUMENTS

| WO | 2007082495 A1 | 7/2007 |
| WO | 2008048708 A2 | 4/2008 |

OTHER PUBLICATIONS

Waybackmachine Actuator date.*
(Continued)

*Primary Examiner* — Unsu Jung
*Assistant Examiner* — Serkan Akar
(74) *Attorney, Agent, or Firm* — Lynn C. Schumacher; Stephen W. Leonard; Hill & Schumacher (57) ABSTRACT

A focused ultrasound system includes an ultrasound transducer configured to emit focused ultrasound energy toward a subject and a positioning system configured to position the ultrasound transducer to localize the focused ultrasound energy within a target location. The positioning system includes a drive apparatus to translate the ultrasound transducer along at least one axis of motion and a motor controller to control the drive apparatus. The focused ultrasound system also includes a control system connected to the motor controller that is programmed to receive imaging/location data from an imaging system, determine positional coordinates of the target location based on the imaging/location data, and register the positional coordinates of the target location with the positioning system. The positional coordinates are sent to the motor controller via an input signal to cause the motor controller to control the drive apparatus so as to translate the ultrasound transducer.

24 Claims, 5 Drawing Sheets

(51) Int. Cl.
  *A61B 19/00*    (2006.01)
  *A61B 17/00*    (2006.01)
  *A61N 7/00*     (2006.01)
  *A61B 8/08*     (2006.01)

(52) U.S. Cl.
  CPC ............... *A61B 2017/0084* (2013.01); *A61B 2017/00106* (2013.01); *A61B 2019/5236* (2013.01); *A61N 2007/0082* (2013.01)

(56) References Cited

U.S. PATENT DOCUMENTS

| | | | |
|---|---|---|---|
| 5,443,068 A * | 8/1995 | Cline et al. | 600/411 |
| 5,743,863 A * | 4/1998 | Chapelon | 601/2 |
| 6,128,522 A | 10/2000 | Acker et al. | |
| 6,432,067 B1 * | 8/2002 | Martin et al. | 601/2 |
| 6,582,381 B1 * | 6/2003 | Yehezkeli et al. | 601/2 |
| 6,589,174 B1 * | 7/2003 | Chopra et al. | 600/411 |
| 6,613,005 B1 * | 9/2003 | Friedman et al. | 601/2 |
| 6,984,209 B2 * | 1/2006 | Hynynen et al. | 600/438 |
| 7,128,711 B2 * | 10/2006 | Medan et al. | 600/439 |
| 7,611,462 B2 * | 11/2009 | Vortman et al. | 600/437 |
| 7,771,418 B2 * | 8/2010 | Chopra et al. | 606/28 |
| 7,822,462 B2 * | 10/2010 | Elias | 600/415 |
| 7,967,816 B2 * | 6/2011 | Ocel et al. | 606/41 |
| 8,002,706 B2 * | 8/2011 | Vortman et al. | 600/437 |
| 2002/0193681 A1 * | 12/2002 | Vitek et al. | 600/411 |
| 2003/0144656 A1 * | 7/2003 | Ocel et al. | 606/41 |
| 2003/0181806 A1 * | 9/2003 | Medan et al. | 600/411 |
| 2003/0187371 A1 * | 10/2003 | Vortman et al. | 601/3 |
| 2004/0236253 A1 * | 11/2004 | Vortman et al. | 601/2 |
| 2005/0004466 A1 * | 1/2005 | Hynynen et al. | 600/449 |
| 2006/0052706 A1 * | 3/2006 | Hynynen et al. | 600/459 |
| 2006/0206105 A1 * | 9/2006 | Chopra et al. | 606/27 |
| 2007/0065420 A1 * | 3/2007 | Johnson | 424/93.7 |
| 2007/0239062 A1 * | 10/2007 | Chopra et al. | 600/549 |
| 2010/0056962 A1 * | 3/2010 | Vortman et al. | 601/2 |
| 2010/0125192 A1 * | 5/2010 | Chopra et al. | 600/411 |

OTHER PUBLICATIONS

Actuator M230_Datasheet.*
Flexible Bellows United.*
Chinzei et al., "Towards MRI guided surgical manipulator", Med Sci Monit, 2001, vol. 7, Issue 1, pp. 153-163.*
Tara technologies, www.taratechnologies.com, 2008.*
Hynynen et al, "MR Imaging-guided Focused Ultrasound Surgery of Fibroadenomas in the Breast: A Feasibility Study", Radiology 2001; 219: pp. 176-185.*

* cited by examiner

COMPUTER CONTROLLED FOCUSED ULTRASOUND POSITIONING SYSTEM FOR SEQUENTIAL BEAM EMITTING TO SONICATE DISCRETE AND INTERLEAVED TISSUE LOCATIONS

CROSS-REFERENCE TO RELATED APPLICATION

The present invention is a non-provisional of, and claims priority to, U.S. Provisional Patent Application Ser. No. 61/115,178, filed Nov. 17, 2008, the disclosure of which is incorporated herein by reference.

BACKGROUND OF THE INVENTION

The present invention relates generally to a system and method of focused ultrasound application and, more particularly, to a focused ultrasound system that provides precise spatial positioning under the guidance of a medical imaging system to deliver focused ultrasound to a target location.

Focused ultrasound therapy involves delivering ultrasound energy to localized regions of tissue from externally (non-invasive) or internally (minimally-invasive) located transducers. The amount of ultrasound energy delivered to tissue dictates the nature of the biologic effect produced at that location. At high intensities with continuous exposure, ultrasound energy can generate enough heat to cause irreversible thermal damage through coagulation. As the exposure is reduced in duty cycle to short pulses, the mechanical energy associated with ultrasound dominates and can be used to generate a range of bio-effects, including: vascular occlusion or hemorrhage, permeation of cells, and tissue-homogenization.

Although the concept of using focused ultrasound energy for therapeutic purposes has been known for many decades, it is desirable to develop further precise control and steering of the acoustic field in the body so as to allow for the use of focused ultrasound in a clinical setting. The integration of therapeutic ultrasound with medical imaging technologies has served to further accelerate the translation of this technology into clinical use. For example, magnetic resonance imaging (MRI)-guided focused ultrasound therapy has gained use as a non-invasive method for thermal tissue coagulation with significant promise for the potentiation of biologic therapies, local delivery of drugs, and targeted heating of tissue for enhanced drug delivery and activation. MRI enables precise targeting of structures for treatment planning, on-line temperature mapping and imaging for monitoring and control of therapy, and results in excellent visualization of the biological response to treatment. That is, an MRI system may be used to plan a focused ultrasound procedure, by performing an initial scan to locate a target tissue region and/or to plan a trajectory between an entry point and the tissue region in preparation for a procedure. Once the target tissue region has been identified, MRI may be used during the procedure, for example, to image the tissue region and/or to guide the trajectory of an external ultrasound beam to a target tissue region being treated. In addition, an MRI system may be used to monitor the temperature of the tissue region during the procedure, for example, to ensure that only the target tissue region is destroyed during an ablation procedure without damaging surrounding healthy tissue.

As the desire to use MRI-guided ultrasound therapy in clinical practice has become more widespread, a need for efficient testing in preclinical models of human disease has been recognized. Such testing commonly involves small animals such as rats and mice, which are used in biomedical research for such preclinical models. However, the small size of these animals makes focused ultrasound experiments difficult. Furthermore, large numbers of animals are required to achieve statistical significance in drug studies, requiring focused ultrasound systems capable of high throughput. To date, there is no focused ultrasound exposure system adapted for use in small animals with the capability to precisely position ultrasound energy to a target location within the animal body, as such ultrasound energy targeting may be required to be accurate within distances of, for example, 0.5 mm or less.

It would therefore be desirable to have a system and method that provides precise spatial positioning capabilities to focused ultrasound systems. It is further desired that such a precise positioning system also be useable with magnetic resonance (MR) imaging guidance to deliver focused ultrasound to a pre-determined target location.

BRIEF DESCRIPTION OF THE INVENTION

Embodiments of the present invention provide a system and method that overcome the aforementioned challenges by including a positioning system capable of precise positioning of an ultrasound transducer. The positioning system is configured to receive positional information on the location of a target location as determined from a magnetic resonance (MR) image and precisely position the ultrasound transducer such that it focuses ultrasound energy on the target location.

In accordance with one aspect of the invention, a focused ultrasound system includes an ultrasound transducer configured to emit a beam of focused ultrasound energy toward a subject and a positioning system configured to position the ultrasound transducer to localize the beam of focused ultrasound energy within a target location in the subject, the positioning system further including a drive apparatus configured to cause translation of the ultrasound transducer along at least one axis of motion and a motor controller configured to control the drive apparatus. The focused ultrasound system also includes a control system connected to the motor controller and connectable to an imaging system, with the control system being programmed to receive imaging or location data from the imaging system, determine positional coordinates of the target location based on the imaging or location data, and register the positional coordinates of the target location with the positioning system. The control system is further programmed to send the positional coordinates to the motor controller via an input signal and cause the motor controller to control the drive apparatus based on the input signal so as to translate the ultrasound transducer, with the translation of the ultrasound transducer occurring prior to, simultaneously with, or subsequent to acquisition of additional imaging data from the imaging system.

In accordance with another aspect of the present invention, a system for positioning an ultrasound transducer operated under medical imaging guidance includes a first non-magnetic actuator to adjust a position of a linear stage in a first horizontal direction, a second non-magnetic actuator to adjust a position of a linear stage in a second horizontal direction, and a third non-magnetic actuator to adjust a position of a rotary stage in a vertical direction. The system also includes a motor controller configured to selectively drive the first, second, and third non-magnetic actuators so as adjust the linear stages and the rotary stage to translate an ultrasound transducer to a desired location in three dimensions relative to a target point and a control system connected to the motor controller. The control system is programmed to receive imaging data from a medical imaging system to identify the one or more target points and send control signals to the motor controller to drive at least one of the first, second, and third non-magnetic actuators to translate the ultrasound transducer to the desired location based on the received imaging data, such that a beam of focused ultrasound energy from ultrasound transducer is localized within the target point.

In accordance with yet another aspect of the present invention, a focused ultrasound system includes an ultrasound transducer configured to emit a beam of focused ultrasound energy toward a subject and a three-axis positioning system configured to position the ultrasound transducer in three dimensions, the three-axis positioning system having a drive apparatus configured to cause translation of the ultrasound transducer in three dimensions and a motor controller configured to control the drive apparatus. The focused ultrasound system also includes a control system connected to the motor controller that is programmed to receive location data identifying at least one target location within the subject, determine positional coordinates of the at least one target location in a three-dimensional space, and register the positional coordinates of the at least one target location with the three-axis positioning system. The control system is further programmed to send motor control signals to activate the three-axis positioning system to translate the ultrasound transducer to at least one desired location so as to localize the beam of focused ultrasound energy within the at least one target location in the subject and activate the ultrasound transducer to emit the ultrasound energy to the at least one target location, with the drive apparatus being configured to translate the ultrasound transducer in increments at or below a resolution of the location data identifying the at least one target location.

Various other features and advantages of the present invention will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION OF THE PREFERRED EMBODIMENT

According to the present invention, a focused ultrasound system is provided that includes a positioning system capable of precise positioning of an ultrasound transducer. In one beneficial application, the focused ultrasound system can be implemented for delivery of focused ultrasound to the brain of small animals. It is also recognized, however, that the focused ultrasound system described here below is also suitable for delivery of focused ultrasound to localized areas of the human body, including areas such as to arms, legs, wrists, and hands and torso. Alternatively this system could also be used on inanimate objects.

Furthermore, while a preferred embodiment of the focused ultrasound system is described below in conjunction with a magnetic resonance imaging (MRI) system as the source of guidance of the focused ultrasound, guidance can also be achieved through use of other medical imaging technologies, such as X-rays, computed tomography, PET, SPECT, or other devices capable of providing anatomical information. Guidance of the focused ultrasound can alternatively be provided by an operator or another computer having data stored thereon.

Figure 1:
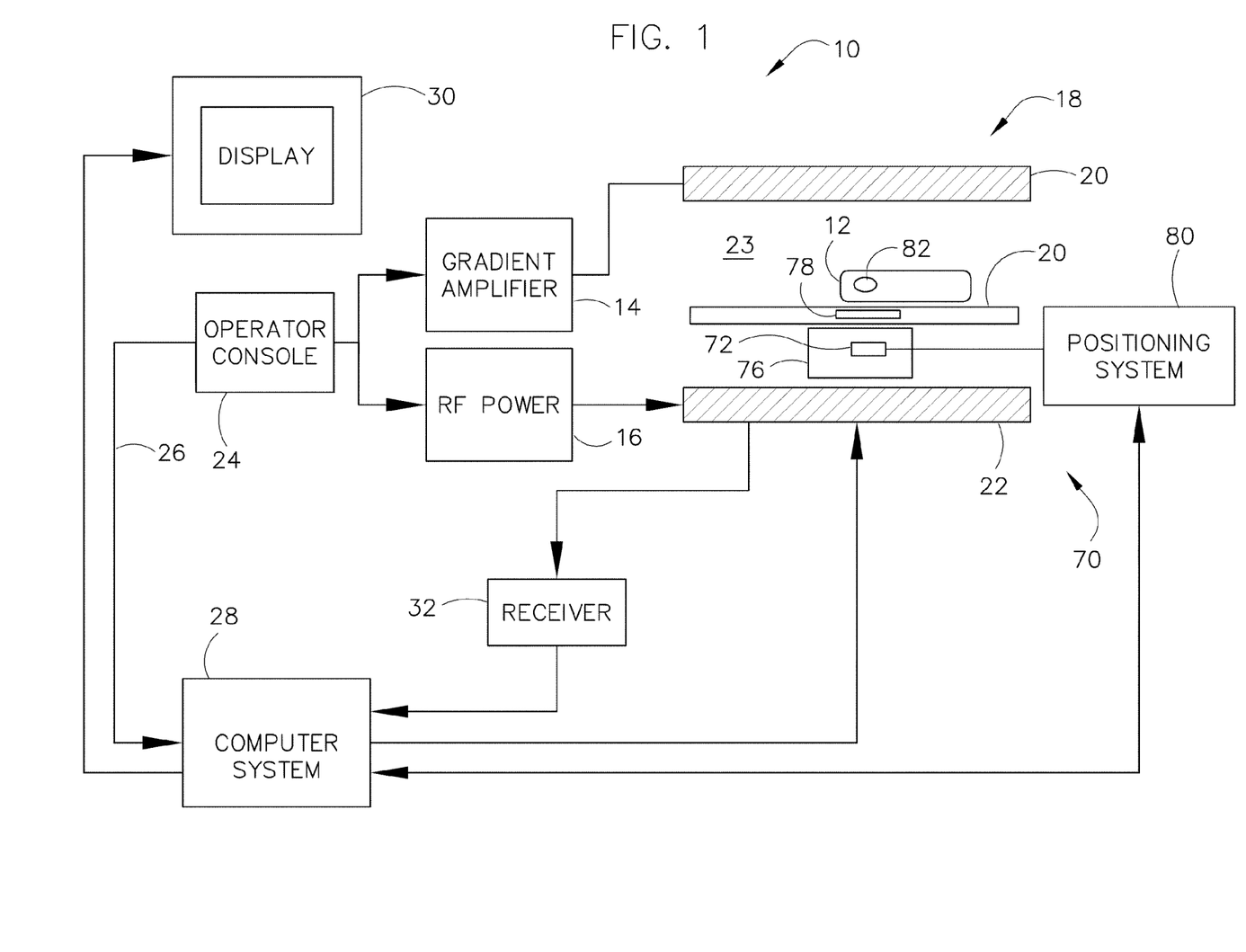
FIG. 1 is a schematic block diagram of an exemplary MR imaging system and focused ultrasound system for use with an embodiment of the present invention.

Referring to FIG. 1, a schematic block diagram of the major components of a preferred magnetic resonance imaging (MRI) system 10 are shown for use with the present invention, according to one embodiment thereof. MRI system 10 employs pulse sequences in the well known manner to rapidly acquire images of a subject 12 or object of interest, which in one application can be a small animal used for focused ultrasound therapy testing. A gradient amplifier 14 and a radiofrequency (RF) power source 16 supply the power for the sequences, which are applied by way of a magnet assembly 18 that includes a polarizing magnet 20 and a RF coil 22. Subject 12 is positioned within a bore 23 of magnet assembly 18 and signals emitted by the excited nuclei in the patient in response to the applied pulse sequences are sensed by the RF coil 22 to acquire MR data.

An operator console 24 is used to control MRI system 10 and communicates through a link 26 with a separate control system 28 (e.g., computer) that enables an operator to control the production and display of images on a display 30. MR data acquired from the subject 12 is sent to a receiver 32, which transfers the data onto control system 28. Control system 28 processes the acquired MR data to, for example, provide anatomical images of subject 12 or provide temperature sensitive images of the subject on display 30.

A focused ultrasound system 70 is positioned, at least in part, adjacent to (or within the bore 23 of) MRI system 10. The focused ultrasound system 70 includes an ultrasound transducer 72 configured to generate and emit focused (or unfocused) ultrasound energy toward subject 12. The focusing can be achieved by mechanical means such as lenses and/or reflectors (not shown), or by manufacturing the transducer element 72 with such a shape that desired focusing will be achieved. Alternatively, ultrasound transducer 72 can be a phased array device capable of electronic focusing and steering of the beam focus.

Ultrasound energy is emitted by ultrasound transducer 72 when electrical energy is transmitted thereto, as is known in the art to control emission of ultrasound energy. The ultrasound energy emitted by ultrasound transducer 72 is transmitted via a coupling element 76 positioned between the ultrasound transducer 72 and the subject 12. In one embodiment, coupling element 76 comprises a water bath (i.e., degassed water) in which ultrasound transducer 72 is submerged such that the generated ultrasound energy will be directed therethrough. An acoustic window 78 is positioned between water bath 76 and subject 12 that allows all or a portion of the ultrasound energy to be transmitted from ultrasound transducer 72 to the target subject as shown in FIG. 1.

While water bath 76 is shown and described in FIG. 1 as comprising the coupling element, it is also envisioned that other low attenuation mediums/mechanisms can comprise the coupling element 76, such as ultrasound gel or another solid, or a flexible water or other liquid coupling. Additionally, while shown in FIG. 1 as being positioned below subject 12, it is envisioned that ultrasound transducer 72 can be located relative to the subject in any of a plurality of positions. Thus, in one embodiment, ultrasound transducer 72 can be located above subject 12, such as in a water cone with a flexible coupling (e.g., flexible membrane tip) to the target region of the subject. In another embodiment, ultrasound transducer 72 can be mounted on the side of subject 12 with a membrane coupling the transducer to the subject. In either of these arrangements, the acoustic coupling can be achieved by direct contact of ultrasound transducer 72 with the subject 12 or with a coupling element 76 such as ultrasound gel or a flexible water coupling.

Referring still to FIG. 1, also included in focused ultrasound system 70 is a positioning system 80 configured to control translation of ultrasound transducer 72 for precise positioning thereof relative to subject 12. As will be explained in greater detail below, positioning system 80 functions to position ultrasound transducer 72 in a desired location relative to one or more target locations 82 that is/are identified in subject 12 by way of an MR image acquired by MRI system 10. That is, control system 28 processes the acquired MR data to reconstruct an MR image, from which one or more target locations 82 are identified. While control system 28 is shown in FIG. 1 as being a single control system shared by MR system 10 and focused ultrasound system 70, it is recognized that separate control systems could be implemented for the two systems, with a control system for MR system 10 in communication with a control system for focused ultrasound system 70.

In operation, control system 28 receives MR data and, based on the MR data, identifies one or more target locations 82. Control system 28 is programmed to determine positional coordinates of the one or more target locations 82 within a coordinate system of the MR imaging space. These positional coordinates are then registered with a coordinate system of positioning system 80. Once registered with a coordinate system of positioning system 80, the positional coordinates of the target location(s) 82 are sent as an input signal to positioning system 80. The positioning system 80 receives the positional coordinates and is actuated by control system 28 to position ultrasound transducer 72 in proximity to target location 82 such that ultrasound energy emitted there from is focused at the target location. That is, the positioning system 80 moves ultrasound transducer 72 such that the focal point of the ultrasound energy generated by the transducer, once turned on, will match the positional coordinates of target location 82. Target location 82 is thus sonicated by ultrasound transducer 72 and heating at target location 82 is monitored via MR image acquisition.

Beneficially, positioning system 80 is controlled by control system 28 to allow for the continuous repositioning of ultrasound transducer 72 during MR image acquisition. This translational control of ultrasound transducer 72 (via positioning system 80) during MR image acquisition allows for the delivery of ultrasound energy to a plurality of target locations or points in rapid succession, such that a plurality of target points in a region of the body can be sonicated/exposed within a short timeframe. Thus, via the control of positioning system 80, ultrasound transducer 72 is translated to deliver focused ultrasound energy to a plurality of target points within subject 12 in any of a point exposure, scanned linear (1D, 2D) exposure, or raster scan (1D, 2D) exposure pattern, or along another continuous trajectory.

According to an embodiment of the invention, control system 28 is programmed to control positioning system 80 and ultrasound transducer 72 so as to cause the ultrasound transducer to sequentially emit beams of focused ultrasound energy according to an interleaved sonication pattern. That is, control system 28 is programmed to control positioning system 80 to translate ultrasound transducer 72 to a series of locations, and for the ultrasound transducer 72 to sequentially emit beams of focused ultrasound energy at each of the series of locations such that each of the locations is sonicated within a specified repetition period. In other words, if a target point requires a sonication every two seconds, the system can scan quickly to multiple points such that each point is exposed every two seconds. Control system 28 is thus programmed to define a repetition period for emitting beams of focused ultrasound energy from ultrasound transducer 72 to a plurality of target locations. Control system 28 is further programmed to cause the motor controller to control the drive apparatus to sequentially translate the ultrasound transducer, such that the beams of focused ultrasound energy are localized within each of the target locations within the repetition period.

Figure 2:
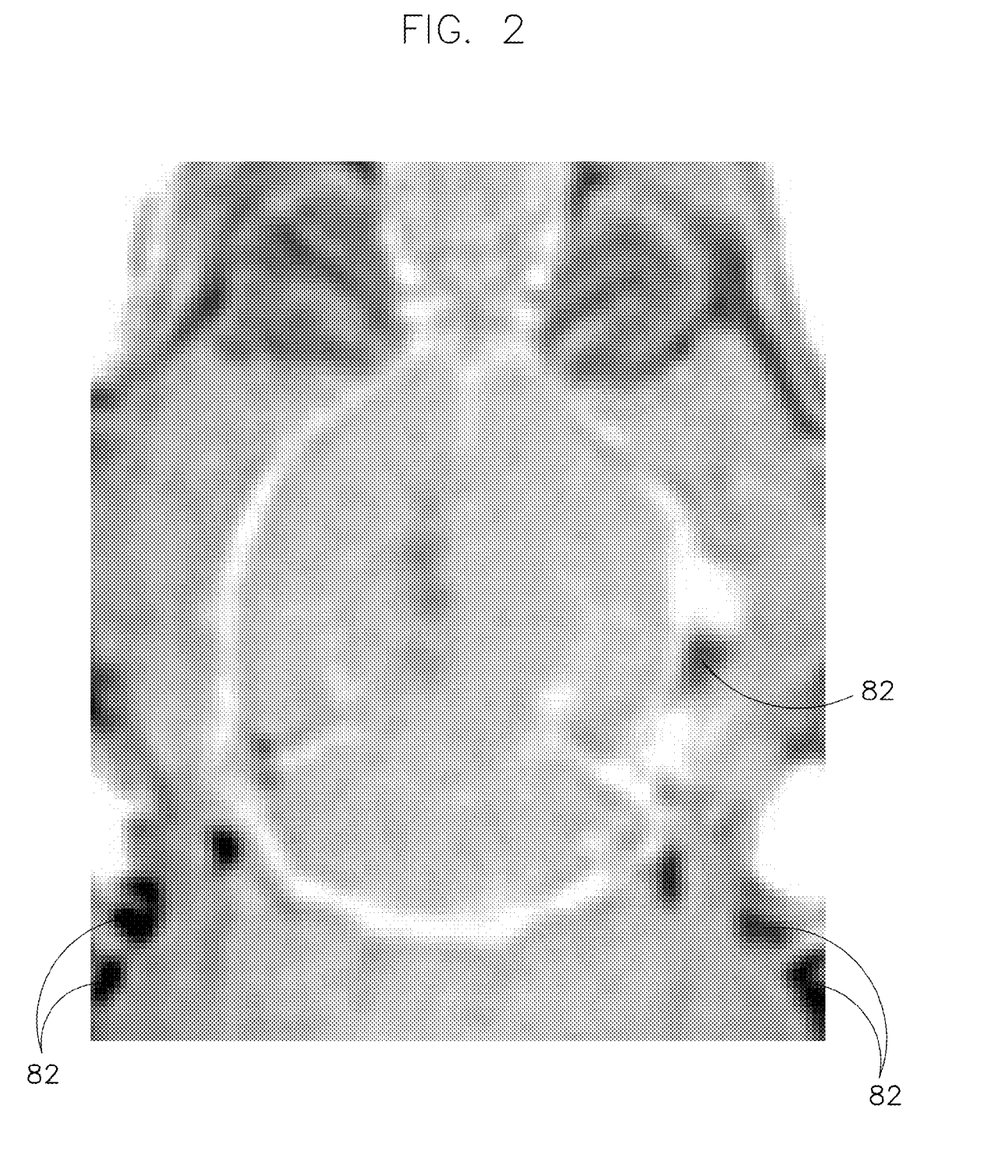
FIG. 2 is a medical image of a rat brain acquired via a scanned linear exposure pattern according to an embodiment of the present invention.

An example of an interleaved sonication pattern enabled by control system 28 is shown in FIG. 2. FIG. 2 shows a scanned linear exposure pattern in a rat brain aimed at opening the blood-brain-barrier (BBB) in a volume of the brain. Positioning system 80 (FIG. 1) repositions ultrasound transducer 72 (FIG. 1) to deliver four ultrasound exposures to target locations 82 in a linear scan that are, for example, 1.5 mm apart, with the exposures occurring approximately 0.25 seconds apart, resulting in an individual repetition frequency (i.e., repetition period) of 1 Hz for each spot. Beneficially, the translation of ultrasound transducer 72 by positioning system 80 (FIG. 1) according to the interleaved sonication approach allows for rapid sonication of a large region that includes a plurality of target locations 82 (e.g., an entire hemisphere of a rat brain), thereby providing a high throughput that is desirable in small animal focused ultrasound studies. The interleaved sonication pattern also reduces the overall injection volume required to cover a series of target locations 82.

Figure 3:
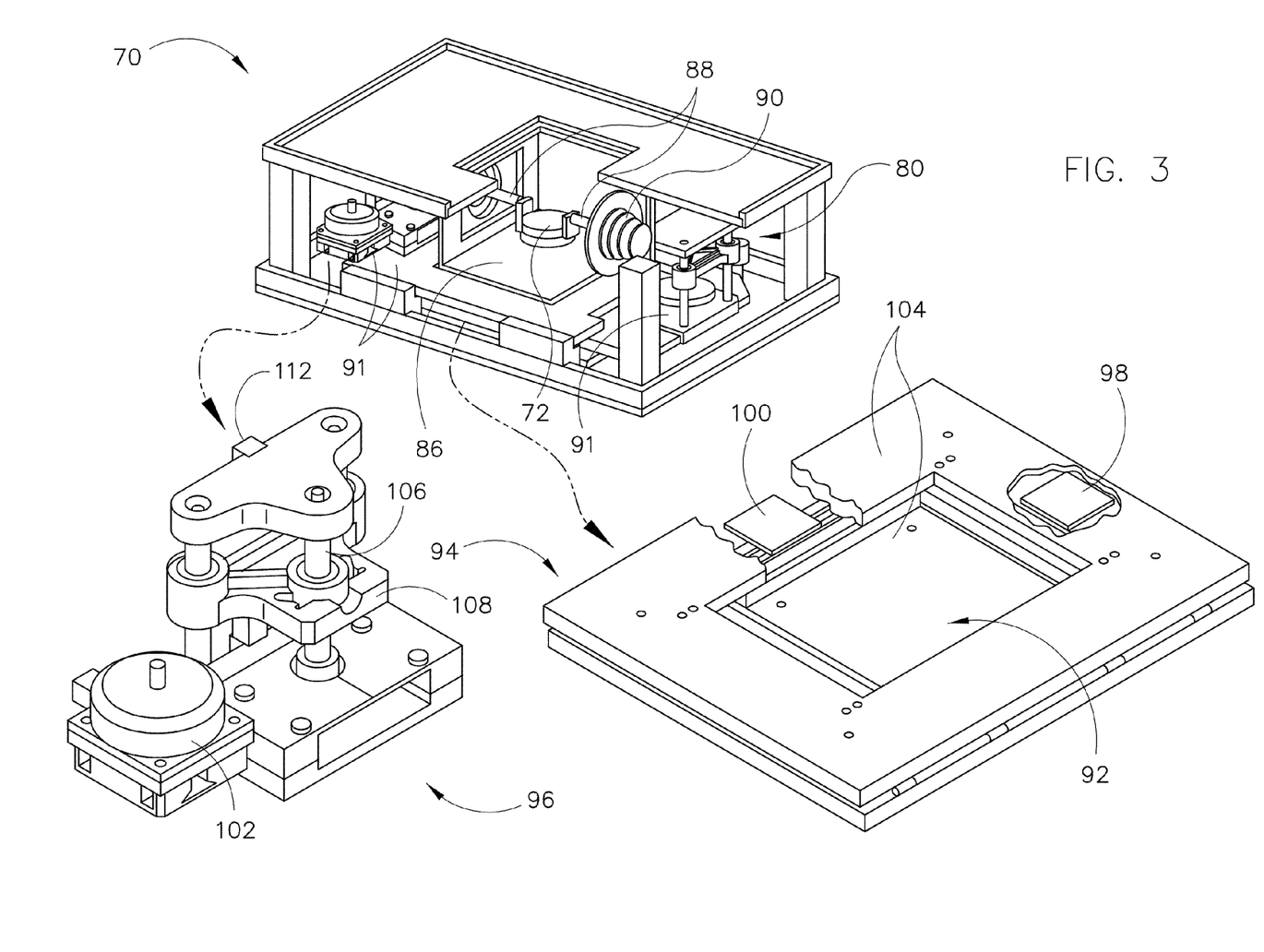
FIG. 3 is an exploded perspective view of a focused ultrasound system according to an embodiment of the present invention.
Figure 4:
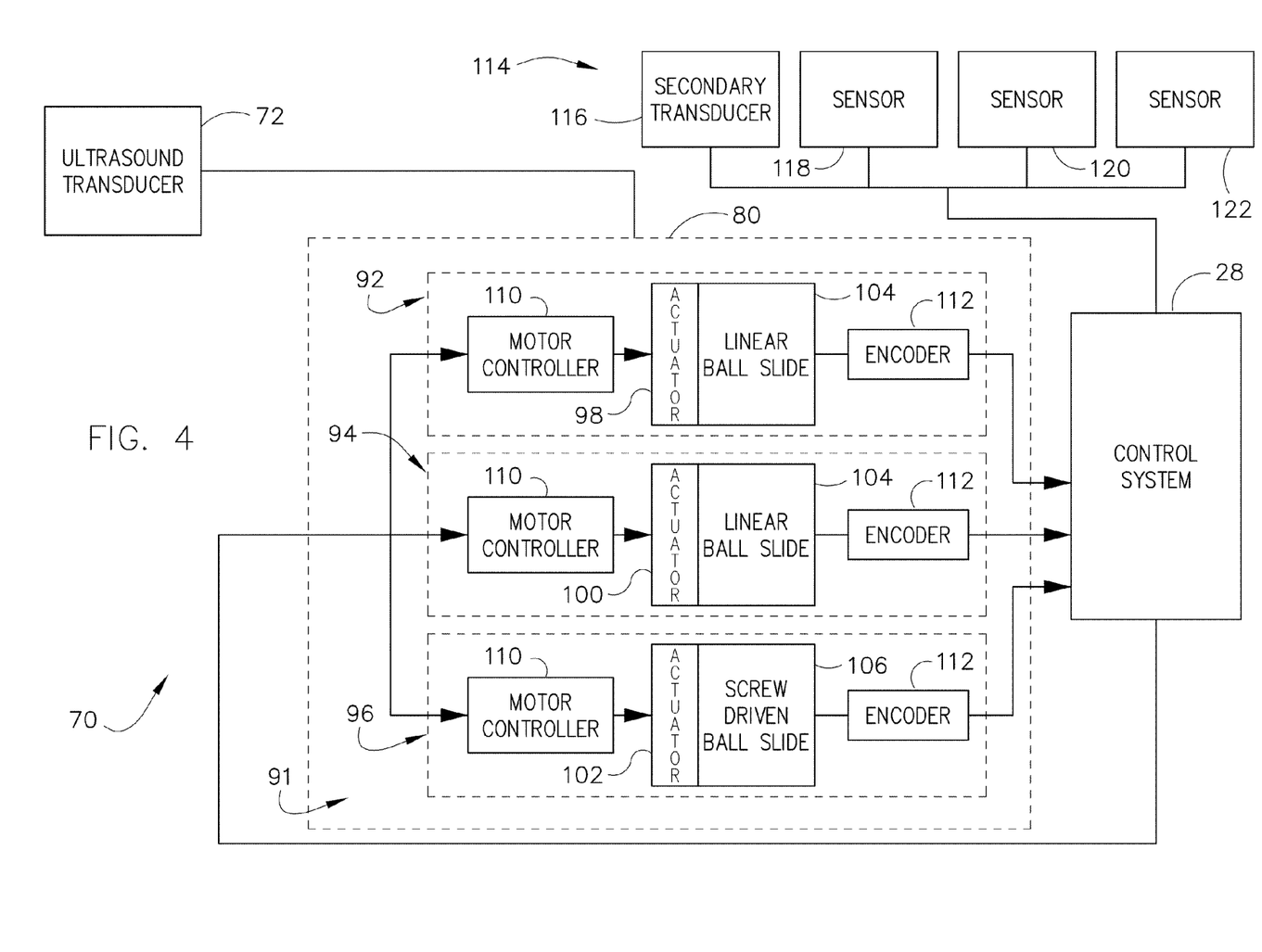
FIG. 4 is a schematic block diagram of a focused ultrasound system according to an embodiment of the present invention.

Referring now to FIGS. 3 and 4, focused ultrasound system 70 is shown in greater detail and according to an exemplary embodiment of the invention. As shown in FIG. 3, focused ultrasound system 70 includes ultrasound transducer 72, positioning system 80, a water tank 86, non-magnetic rods 88, and rubber bellows 90. The, ultrasound transducer 72 is supported in water tank 86 by the two non-magnetic rods 88, which extend outside of the tank through flexible rubber bellows 90 that provide a water-tight seal through which the non-magnetic rods enter/exit two sides of water tank 86. Beneficially, suspension of ultrasound transducer 72 in water tank 86 by way of non-magnetic rods 88 extending outward in two directions allows for improved stability and uniform movement of the ultrasound transducer. It is recognized, however, that other embodiments of the invention could be constructed having non-magnetic rods 88 that enter/exit from a single side of water tank 86.

As shown in FIG. 3, focused ultrasound system 70 includes a positioning system 80 having three degrees of freedom. That is, positioning system 80 is configured to allow ultrasound transducer 72 to be moved in a horizontal plane defined by the x axis and y axis, as well as vertically out of this plane, along the z axis. It is further envisioned, however, that positioning system 80 can also provide a greater or lesser number of degrees of freedom. Positioning system 80 could allow four or five degrees of freedom by enabling rotation of ultrasound transducer 72 about one or both of the x and y axes (e.g., by addition of a rotational-type ultrasonic motor), or conversely, could be limited to only two degrees of freedom by limiting linear translation to the horizontal plane.

The amount of translation provided by positioning system 80 along each of the x, y, and z axes can also vary. When focused ultrasound system 70 is designed for use with focused ultrasound experiments on small animals, for example, travel length of the positioning system 80 can be limited to 5 cm in the horizontal and 2.5 cm vertical. It is also envisioned, however, that the travel length provided by positioning system 80 could be extended to over 20 cm when ultrasound system 70 is designed for delivery of focused ultrasound to localized areas of the human body.

As shown in FIGS. 3 and 4, positioning system 80 includes a drive apparatus 91 comprised of a plurality of linear stages 92, 94, 96 driven by ultrasonic actuators 98, 100, 102 (i.e., ultrasonic motors). Each of the ultrasonic actuators 98, 100, 102 is coupled to a respective linear stage 92, 94, 96 to selectively cause translation thereof. Specifically, ultrasonic actuators 98, 100, 102 incorporate a piezoelectric material, such as lead zirconate titanate, lithium niobate, or another single crystal material, and make use of resonance to amplify the vibration of contacting components (i.e., linear stage 92, 94, 96) and impart motion thereto.

The plurality of linear stages 92, 94, 96 and ultrasonic actuators 98, 100, 102 allows for translation and positioning of ultrasound transducer 72 to various desired locations in three dimensional space. For controlling translation of ultrasound transducer 72 in the horizontal plane defined by the x and y axes, first and second linear stages 92, 94 (i.e., horizontal stages) are included in positioning system 80. Each of the first and second linear stages 92, 94 includes a corresponding ultrasonic actuator 98, 100 that is coupled thereto, such that positioning system 80 can translate ultrasound transducer 72 along the x and y axes. According to an exemplary embodiment, the design of the x and y linear stages 92, 94 is intended to provide a low profile stage to conserve space in the bore of an imaging system, such as the MR imaging system 10 of FIG. 1. Thus, in one embodiment, and as shown in FIG. 3, linear stages 92, 94 comprise linear ball-slides 104 on which ultrasonic actuators 98, 100 are mounted to cause movement thereof; however, those skilled in the art will readily appreciate that a number of alternative linear stage designs incorporating high stability and low friction can also be used in conjunction with the actuators.

Referring still to FIG. 3, a third linear stage 96 (i.e., vertical stage) is also included in positioning system 80 for controlling translation of ultrasound transducer 72 in the vertical plane, along the z axis. An ultrasonic actuator 102 is coupled to linear stage 96 to control vertical motion of the ultrasound transducer 72. In an exemplary embodiment, linear stage 96 comprises a rotary-type stage that causes vertical translation along a linear path in a smooth, controlled fashion. As shown in FIG. 3, rotary-type stage 96 includes a lead-screw driven ball slide 106 that causes vertical motion of a plate 108. A rotary-type stage 96 is located on either side of water tank 86, with the plate 108 of each stage being attached to non-magnetic rods 88 attached to ultrasound transducer 72. The two vertical rotary stages 96 are linked through mechanical means, such as a belt or chain (not shown), to provide smooth and stable translation of ultrasound transducer 72. While linear stage 96 is shown in FIG. 3 constructed as a rotary-type stage being in the form of a lead-screw driven ball slide 106 and plate 108, it is recognized that a number of alternative linear stage designs incorporating high stability and low friction can also be used, such as the linear ball-slides implemented for horizontal stages 92, 94.

As shown in FIG. 4, a motor controller 110 is also included in positioning system 80 corresponding to each stage 92, 94, 96, with each motor controller 110 being operationally connected to the ultrasonic actuators 98, 100, 102 to drive the actuators for translating the stages 92, 94, 96. The motor controllers 110 receive signals from control system 28 that contain positional coordinates of where ultrasound transducer 72 is to be positioned for emission of ultrasound energy to a target location, as described above. The motor controllers 102 are then activated to drive ultrasonic actuators 98, 100, 102 to cause translation of stages 92, 94, 96 in positioning system 80. In one embodiment, motor controllers 110 are configured to drive ultrasonic actuators 98, 100, 102 via sinusoidal voltage signals at a frequency much lower than the bandwidth of the MRI system (e.g., approximately 40-100 kHz), thus enabling good isolation between the MRI system 10 (shown in FIG. 1) and the focused ultrasound system 70.

Also included in positioning system 80 are optical encoders 112 associated with each of ultrasonic linear stages 92, 94, 96 to provide for precise motion control. Similar to the ultrasonic actuators 98, 100, 102, the optical encoders 112 can also operate with signals in the form of sinusoidal voltages at a frequency of, for example, approximately 40-100 kHz. The optical encoders 112 are configured to monitor the location of positioning system 80 by sensing linear translation of stages 92, 94, 96. That is, a precise position of ultrasound transducer 72 within the coordinate system of positioning system 80 can be determined by way of optical encoders 112 and their detection of any change in the position of the linear stages 92, 94, 96.

In response to a measured translation, optical encoders 112 output a digital signal indicative of an amount of translation. The monitored translation measured by optical encoders 112 is sent as feedback to control system 28 via the output digital signal. The control system 28 is programmed to receive the measured translation feedback from optical encoders 112 to determine any adjustment of positioning system 80 that may be necessary to compensate for any displacement in the position of stages 92, 94, 96 that may have been caused by the main magnetic field of the MRI magnet, a fluctuating magnetic field of the gradient coils, or another external force. The measured translation feedback received by control system 28 is processed and, in response thereto, control signals are generated and sent to motor controllers 110. The motor controllers 110 can then drive the stages 92, 94, 96 to translate ultrasound transducer 72 along one or more axes so as to "calibrate" positioning system 80 and return the ultrasound transducer 72 to a proper location and negate the effects of external magnetic field influence.

The plurality of ultrasonically actuated linear stages 92, 94, 96 incorporated into focused ultrasound system 70 enables fast sequential ultrasound application via ultrasound transducer 72 to the target locations 82 in subject 12 (shown in FIG. 1). Translating of stages 92, 94, 96 by ultrasonic actuators 98, 100, 102 allows for positioning system 80 to translate ultrasound transducer 72 in three dimensions at a speed of, for example, 1 mm/s along the vertical axis and 20 mm/s along the horizontal axes. This allows for repositioning of ultrasound transducer 72 such that it can deliver ultrasound energy at up to 10 spots (i.e. target locations) per second (for exposures at 1.08 MHz with a burst duration of 10 ms and a repetition frequency of 1 Hz) in a point exposure, scanned linear (1D, 2D) exposure, raster scan (1D, 2D) exposure pattern, or other continuous path pattern, as set forth in detail above. The level of repeatability and speed achieved with positioning system 80 thus enables high throughput investigation of, for example, drug delivery to the brain of a small animal subject using focused ultrasound.

Additionally, the incorporation of ultrasonically actuated linear stages 92, 94, 96 into focused ultrasound system 70 allows for precision motion control of ultrasound transducer 72. That is, coupling of ultrasonic actuators 98, 100, 102 to linear stages 92, 94 (for movement in each horizontal axis) and rotary-type stage 96 (for movement along a vertical axis) allows for precision positioning of ultrasound transducer 72 in three dimensions. The positioning system 80 is capable of positioning ultrasound transducer 72 along the x, y, and z axes with a spatial accuracy of 0.3 mm or less, such as down to increments of 50 microns. Such precise positioning allows for accurate and consistent delivery of focused ultrasound energy to multiple target locations 82 along a desired trajectory.

As set forth above, and according to an exemplary embodiment of the invention, focused ultrasound system 70 is operated under the guidance of an MRI system, receiving imaging data therefrom in order to identify and locate target locations in the subject. When used in conjunction with a MRI system, focused ultrasound system 70 is formed substantially of non-magnetic materials. In order for focused ultrasound system 70 to be used near or within MRI system 10 (shown in FIG. 1), its operations cannot be greatly affected by a magnetic field, and conversely, it cannot have too great an effect on the magnetic field of the MRI system. Therefore, stages 92, 94, 96 and ultrasonic actuators 98, 100, 102 are formed of MRI compatible materials, such that it can be placed in or near the MRI system. Similarly, rods 88 and water tank are also formed of MRI compatible materials. These compatible materials can include, but are not limited to, aluminum, brass, plastic, ceramics, and glass.

The high level of MRI-compatibility of focused ultrasound system 70 allows for simultaneous MR imaging and motion of positioning system (to reposition ultrasound transducer 72) without mutual interference. As would be understood by one skilled in the art, control system 28 used to control the motion of the stages 92, 94, 96 (via motor controllers 102) is preferably located outside the room containing the MRI system 10 (shown in FIG. 1), with cables connecting the control system 28 to focused ultrasound system 70. Appropriate filters and grounding of the cables is implemented to maintain adequate isolation of the MRI system from RF noise.

Beneficially, as focused ultrasound system 70 and MR imaging can occur simultaneously, MR imaging can be employed to monitor heating at the target location 82 during sonication, such that a timely determination can be made as to when the target location has been sufficiently sonicated. Upon such a determination, positioning system 80 functions to move the transducer to a next target location with minimal delay. Fast sequential scanning of multiple target points can thereby be performed, allowing for increased throughput.

Referring still to FIG. 4, according to an exemplary embodiment of the invention, focused ultrasound system 70 incorporates one or more additional transducers or sensors 114 that acquire sonication related parameters that can be used for controlling application of ultrasound energy to target location(s) 82. The sonication related parameters acquired by these transducers or sensors 114 are transmitted to control system 28 for purposes of modifying the application of focused ultrasound energy to the target areas 82 by ultrasound transducer 72. According to one embodiment, the measured sonication related parameters are monitored and analyzed by control system 28 to control emission of the beams of focused ultrasound energy from the ultrasound transducer 72. According to another embodiment, the measured sonication related parameters are monitored and analyzed by control system 28 and then displayed to an operator (such as by display 30, FIG. 1) so as to guide the operator in conducting the sonication procedure.

In one embodiment of the focused ultrasound system 70, a secondary transducer 116 is provided that is configured to transmit and receive ultrasound pulses for the purposes of ultrasound imaging of the target location. Ultrasound echoes received by the secondary transducer 116 are transmitted to control system 28, where the echoes can be processed into ultrasound images that, for example, supplement acquired MR images. Based on the ultrasound images acquired via secondary transducer 116, the control system 28 can control the emission of ultrasound energy from ultrasound transducer 72 or display the ultrasound images for the operator.

In another embodiment of the focused ultrasound system 70, a sensor 118 is provided in addition to the therapeutic ultrasound transducer 72 that is configured to measure acoustic emissions related to gas bubble activity or other phenomena within the subject 12 during exposure of focused ultrasound with the therapeutic transducer. Sensor 118 measures oscillation, growth, and/or cavitation of gas bubbles for purposes of monitoring tissue ablation, for example. The measured gas bubble activity is transmitted to control system 28 for monitoring/analysis, with control system 28 subsequently controlling the emission of ultrasound energy from ultrasound transducer 72 or displaying a value/level of the gas bubble activity to the operator.

In another embodiment of the focused ultrasound system 70, a means for measuring the forward and reflected electrical power transmitted to the ultrasound transducer 72 is provided. For example, a sensor 120 is provided having a temporal resolution sufficient to characterize individual forward and reflected RF pulses (<100 μs) transmitted to the ultrasound transducer 72, thereby enabling accurate characterization of the acoustic power transmitted to the target region. The measured forward and reflected electrical power transmitted to the ultrasound transducer 72 is provided to control system 28 for monitoring/analysis, with control system 28 subsequently controlling the emission of ultrasound energy from ultrasound transducer 72 or displaying a value/level of the forward and reflected electrical power to the operator.

In another embodiment of the focused ultrasound system 70, a sensor 122 is provided for measuring a physiological parameter of the subject undergoing the focused ultrasound procedure. Physiological sensor 122 may constitute any one of a number of sensors for measuring a desired physiological parameter. Thus, for example, physiological sensor 122 may be in the form of a fiber-optic temperature sensor located on the skin surface of the subject or within a body cavity of the subject. Fiber-optic temperature sensor 122 measures the temperature of the subject, which is then transmitted to control system 28 for monitoring/analysis, with control system 28 subsequently controlling the emission of ultrasound energy from ultrasound transducer 72 or displaying the temperature of the subject to the operator.

Figure 5A:
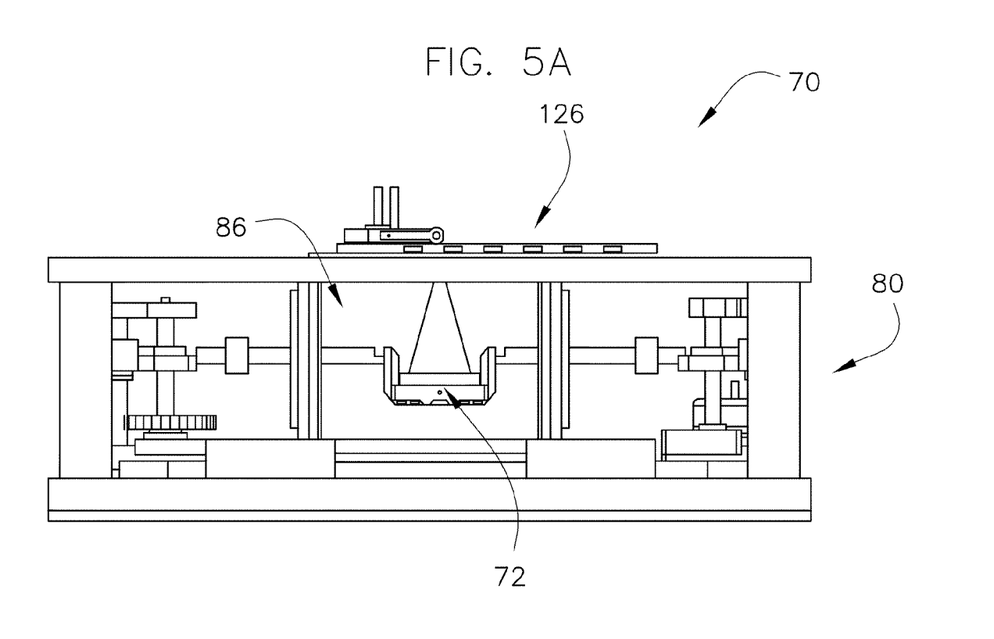
FIGS. 5A and 5B show two embodiments of a focused ultrasound system in which the transducer is arranged above and below the subject receiving an exposure according to embodiments of the present invention.
Figure 5B:
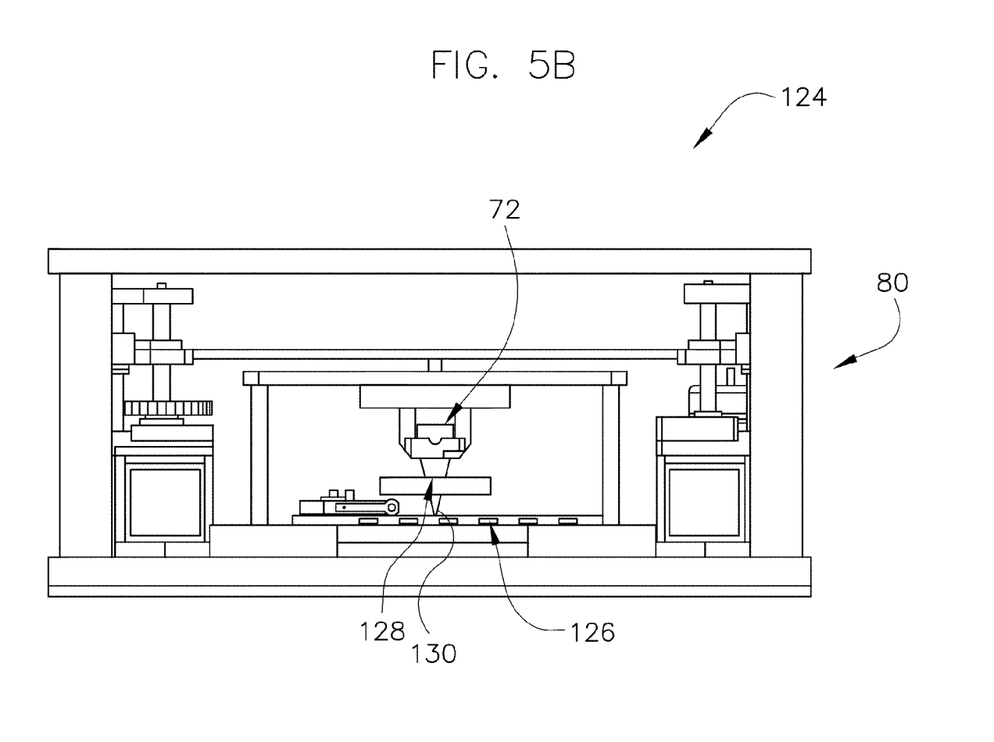

Referring now to FIGS. 5A and 5B, two embodiments of the focused ultrasound system are shown (for purposes of comparison) in which the transducer is located either above or below the subject being exposed to ultrasound energy. FIG. 5A shows a side view of a focused ultrasound system 70 where the ultrasound transducer 72 is located below the subject being exposed to ultrasound energy, such as is shown in FIG. 3. FIG. 5B shows a side view of a focused ultrasound system 124 where the ultrasound transducer 72 is located above the subject being exposed to ultrasound energy. The two embodiments of the focused ultrasound system share similar components for controlling motion along the vertical and horizontal axes (i.e., positioning system 80, as explained in detail in FIG. 3) and a similar holder 126 for positioning the subject in a desired position. The transducer 72 is coupled to the subject using a medium which could be a gel, water, oil, or other material that supports ultrasound propagation. Depending on the positioning of the focused ultrasound system 70, 124 above or below the subject, the nature of the coupling tank or reservoir is slightly different based on the geometrical configuration of the transducer and the subject. With respect to the embodiment of focused ultrasound system 70 shown in FIG. 5A, the coupling element may be in the form of a water tank 86, for example. The embodiment of the focused ultrasound system 70 with the transducer 72 below the subject is suitable for general purpose usage with a range of subject types and size, and offers the most flexibility. With respect to the embodiment of focused ultrasound system 124 shown in FIG. 5B, the coupling element may be in the form of a water cone 128 with a flexible coupling or flexible membrane tip 130. The embodiment of the focused ultrasound system 124 with the transducer 72 above the subject is useful for small subjects such as rodents, in which the target is the head, and a standard stereotaxic arrangement is desired.

A technical contribution for the disclosed method and apparatus is that it provides for computer implemented spatial positioning of an ultrasound transducer under the guidance of a medical imaging system to deliver focused ultrasound to a target location.

Therefore, according to one embodiment of the present invention, a focused ultrasound system includes an ultrasound transducer configured to emit a beam of focused ultrasound energy toward a subject and a positioning system configured to position the ultrasound transducer to localize the beam of focused ultrasound energy within a target location in the subject, the positioning system further including a drive apparatus configured to cause translation of the ultrasound transducer along at least one axis of motion and a motor controller configured to control the drive apparatus. The focused ultrasound system also includes a control system connected to the motor controller and connectable to an imaging system, with the control system being programmed to receive imaging or location data from the imaging system, determine positional coordinates of the target location based on the imaging or location data, and register the positional coordinates of the target location with the positioning system. The control system is further programmed to send the positional coordinates to the motor controller via an input signal and cause the motor controller to control the drive apparatus based on the input signal so as to translate the ultrasound transducer, with the translation of the ultrasound transducer occurring prior to, simultaneously with, or subsequent to acquisition of additional imaging data from the imaging system.

According to another embodiment of the present invention, a system for positioning an ultrasound transducer operated under medical imaging guidance includes a first non-magnetic actuator to adjust a position of a linear stage in a first horizontal direction, a second non-magnetic actuator to adjust a position of a linear stage in a second horizontal direction, and a third non-magnetic actuator to adjust a position of a rotary stage in a vertical direction. The system also includes a motor controller configured to selectively drive the first, second, and third non-magnetic actuators so as adjust the linear stages and the rotary stage to translate an ultrasound transducer to a desired location in three dimensions relative to a target point and a control system connected to the motor controller. The control system is programmed to receive imaging data from a medical imaging system to identify the one or more target points and send control signals to the motor controller to drive at least one of the first, second, and third non-magnetic actuators to translate the ultrasound transducer to the desired location based on the received imaging data, such that a beam of focused ultrasound energy from ultrasound transducer is localized within the target point.

According to yet another embodiment of the present invention, a focused ultrasound system includes an ultrasound transducer configured to emit a beam of focused ultrasound energy toward a subject and a three-axis positioning system configured to position the ultrasound transducer in three dimensions, the three-axis positioning system having a drive apparatus configured to cause translation of the ultrasound transducer in three dimensions and a motor controller configured to control the drive apparatus. The focused ultrasound system also includes a control system connected to the motor controller that is programmed to receive location data identifying at least one target location within the subject, determine positional coordinates of the at least one target location in a three-dimensional space, and register the positional coordinates of the at least one target location with the three-axis positioning system. The control system is further programmed to send motor control signals to activate the three-axis positioning system to translate the ultrasound transducer to at least one desired location so as to localize the beam of focused ultrasound energy within the at least one target location in the subject and activate the ultrasound transducer to emit the ultrasound energy to the at least one target location, with the drive apparatus being configured to translate the ultrasound transducer in increments at or below a resolution of the location data identifying the at least one target location.

The present invention has been described in terms of the preferred embodiment, and it is recognized that equivalents, alternatives, and modifications, aside from those expressly stated, are possible and within the scope of the appending claims.

What is claimed is:

1. A focused ultrasound system for localizing a beam of focused ultrasound energy within a plurality of target locations in a subject, the focused ultrasound system comprising:
    an ultrasound transducer configured to emit a beam of focused ultrasound energy toward the subject;
    a positioning system configured to position the ultrasound transducer to localize the beam of focused ultrasound energy within the plurality of target locations in the subject, the positioning system comprising:
        a drive apparatus including an actuator to cause translation of the ultrasound transducer along at least one axis of motion; and
        one or more motor controllers configured to control the drive apparatus; and
    a computer connected to each motor controller and to the ultrasound transducer, the computer programmed to:
        define a repetition period for emitting beams of focused ultrasound energy from the ultrasound transducer to the plurality of discrete target locations;
        send control signals to each motor controller to control the drive apparatus to sequentially translate the ultrasound transducer to a series of transducer locations during each repetition period, such that at each transducer location, ultrasound energy emitted by the ultrasound transducer is focused to a respective discrete target location; and
        control the ultrasound transducer to sequentially emit the beams of focused ultrasound energy during each repetition period, such that a beam of focused ultrasound energy is emitted at each transducer location, and such that each of the discrete target locations is sonicated during each repetition period according to an interleaved sonication pattern.

2. The focused ultrasound system of claim 1 wherein the drive apparatus comprises a non-magnetic drive apparatus including:
   a first linear stage configured to adjust a position of the ultrasound transducer in a first horizontal direction;
   a second linear stage configured to adjust a position of the ultrasound transducer in a second horizontal direction;
   a third linear stage configured to adjust a position of the ultrasound transducer in a vertical direction; and
   an ultrasonic motor corresponding to each of the first linear stage, the second linear stage, and the third linear stage, the ultrasonic motors configured to selectively translate the first linear stage, the second linear stage, and the third linear stage so as to position the ultrasound transducer to localize the beam of focused ultrasound energy within the target location in the subject.

3. The focused ultrasound system of claim 2 wherein the first and second linear stages comprise linear ball slides and wherein the third linear stage comprises a rotary-type stage.

4. The focused ultrasound system of claim 1 wherein the positioning system is configured to control positioning of the ultrasound transducer in increments at or below a resolution of the imaging or location data used to define the target location.

5. The focused ultrasound system of claim 1 further comprising a water tank, wherein the ultrasound transducer is enclosed within the water tank, and the drive apparatus is located outside the water tank.

6. The focused ultrasound system of claim 5 further comprising:
   a plurality of rods configured to connect the ultrasound transducer to the drive apparatus, the plurality of rods entering at least one side of the water tank; and
   a flexible bellows configured to maintain a watertight seal where the plurality of rods enter the at least one side of the water tank.

7. The focused ultrasound system of claim 1 further comprising a water cone having a flexible membrane at a tip thereof positioned between the ultrasound transducer and the subject such that the beam of focused ultrasound energy is transmitted therethrough.

8. The focused ultrasound system of claim 1 further comprising an optical encoder connected to the drive apparatus to measure the translation of the ultrasound transducer.

9. The focused ultrasound system of claim 1 wherein the plurality of target locations were identified by way of an image acquired by an MR imaging system; and
   wherein the motor controller is configured to generate a sinusoidal voltage output to drive the drive apparatus, the sinusoidal voltage output having a frequency below an operational frequency of the MR imaging system so as to minimize interference therebetween during imaging.

10. The focused ultrasound system of claim 1 wherein the computer is programmed to:
   monitor and analyze at least one sonication related parameter during exposure of the subject to the beam of focused ultrasound energy; and
   based on the at least one sonication related parameter, control emission of the beams of focused ultrasound energy from the ultrasound transducer or display a value of the at least one sonication related parameter to an operator.

11. The focused ultrasound system of claim 10 further comprising a secondary transducer configured to measure acoustic emissions related to gas bubble activity within the subject during exposure to the beam of focused ultrasound energy; and
   wherein the computer is programmed to control emission of the beams of focused ultrasound energy from the ultrasound transducer or display a value of the acoustic emissions to an operator based on the measured acoustic emissions.

12. The focused ultrasound system of claim 10 further comprising a secondary transducer configured to transmit ultrasound pulses and receive ultrasound echoes for ultrasound imaging of the target location; and
   wherein the computer is programmed to control emission of the beams of focused ultrasound energy from the ultrasound transducer or display a value of the ultrasound echoes to an operator based on the received ultrasound echoes.

13. The focused ultrasound system of claim 10 further comprising a means for measuring forward and reflected electrical power transmitted to the ultrasound transducer, the means for measuring forward and reflected electrical power configured to have a temporal resolution sufficient for characterizing individual RF pulses; and
   wherein the computer is programmed to control emission of the beams of focused ultrasound energy from the ultrasound transducer or display a value of the forward and reflected electrical power to an operator based on the measured forward and reflected electrical power transmitted to the ultrasound transducer.

14. The focused ultrasound system of claim 10 further comprising a fiber-optic temperature sensor configured to measure a temperature of the subject; and
   wherein the computer is programmed to control emission of the beams of focused ultrasound energy from the ultrasound transducer or display a value of the temperature to an operator based on the measured temperature of the subject.

15. A system for localizing a beam of focused ultrasound energy within a plurality of target points in a subject, the system comprising:
   a first non-magnetic actuator to adjust a position of a first linear stage in a first horizontal direction;
   a second non-magnetic actuator to adjust a position of a second linear stage in a second horizontal direction; and
   a third non-magnetic actuator to adjust a position of a third linear stage in a vertical direction;
   one or more motor controllers configured to selectively drive the first, second, and third non-magnetic actuators so as adjust the linear stages, thereby translating an ultrasound transducer to a desired location in three dimensions relative to the plurality of discrete target points; and
   a computer connected to each motor controller and to an ultrasound transducer, the computer programmed to:
      define a repetition period for emitting beams of focused ultrasound energy from the ultrasound transducer to the plurality of discrete target points; and
      send control signals to each motor controller to control the first, second, and third non-magnetic actuators to sequentially translate the ultrasound transducer to desired locations in three dimensions during each repetition period, such that at each transducer location, ultrasound energy emitted by the ultrasound transducer is directed to a respective discrete target location; and
      control the ultrasound transducer to sequentially emit the beams of focused ultrasound energy during each repetition period, such that a beam of focused ultrasound energy is emitted at each transducer location, and such that each of the plurality of discrete target points is sonicated during each repetition period according to an interleaved sonication pattern.

16. The system of claim 15 wherein each of the first, second, and third non-magnetic actuators comprises an ultrasonic piezoelectric actuator.

17. The system of claim 15 wherein the first, second, and third non-magnetic actuator actuators are configured to adjust the linear stages with a precision of between 50 microns and 0.3 millimeters.

18. The system of claim 15 further comprising: a water tank configured to receive the ultrasound transducer therein, the ultrasound transducer being enclosed in the water tank and the first, second, and third non-magnetic actuators and the linear stages being located outside the water tank;
a plurality of rods configured to connect the ultrasound transducer to the linear stages and the rotary stage, the plurality of rods entering at least one side of the water tank; and
a flexible bellows configured to maintain a watertight seal where the plurality of rods enter the at least one side of the water tank.

19. The system of claim 15 further comprising an optical encoder coupled to each of the linear stages to generate feedback on a measured movement of the ultrasound transducer.

20. The system of claim 15 wherein the computer is further programmed to send control signals to the one or more motor controllers to drive at least one of the first, second, and third actuators to translate the ultrasound transducer during acquisition of imaging data by the medical imaging system.

21. A focused ultrasound system for localizing a beam of focused ultrasound energy within a plurality of target locations in a subject, the focused ultrasound system comprising:
an ultrasound transducer configured to emit a beam of focused ultrasound energy toward a subject;
a three-axis positioning system configured to position the ultrasound transducer in three dimensions, the three-axis positioning system comprising; a drive apparatus including an actuator to cause translation of the ultrasound transducer in three dimensions and one or more motor controllers configured to control the drive apparatus; and
a computer connected to each motor controller and to the ultrasound transducer, the computer programmed to:
define a repetition period for emitting beams of focused ultrasound energy from the ultrasound transducer to the plurality of discrete target locations;
send control signals to each motor controller to control the drive apparatus to sequentially translate the ultrasound transducer to a series of transducer locations during each repetition period, such that at each transducer location, ultrasound energy emitted by the ultrasound transducer is directed to a respective discrete target location; and
control the ultrasound transducer to sequentially emit the beams of focused ultrasound energy during each repetition period, such that a beam of focused ultrasound energy is emitted at each transducer location, and such that each of the discrete target locations is sonicated during each repetition period according to an interleaved sonication pattern.

22. The focused ultrasound system of claim 21 wherein the drive apparatus comprises a non-magnetic drive apparatus including:
a first linear stage configured to adjust a position of the ultrasound transducer in a first horizontal direction;
a second linear stage configured to adjust a position of the ultrasound transducer in a second horizontal direction;
a rotary stage configured to adjust a position of the ultrasound transducer in a vertical direction; and
an ultrasonic motor corresponding to each of the first linear stage, the second linear stage, and the rotary stage, the ultrasonic motors configured to selectively translate the first linear stage, the second linear stage, and the rotary stage so as to position the ultrasound transducer to the at least one desired location.

23. The focused ultrasound system of claim 21 wherein the computer is programmed to send motor control signals to activate the three-axis positioning system to translate the ultrasound transducer to the at least one desired location concurrently with acquisition of additional imaging data.

24. The focused ultrasound system of claim 1 wherein the plurality of discrete target locations are positioned along a linear scan path, with the computer being programmed to cause the motor controller to control the drive apparatus to sequentially translate the ultrasound transducer to each discrete target location along the linear scan path such that the beams of focused ultrasound energy are localized within each of the discrete target locations along the linear scan path within each repetition period.

* * * * *